(12) United States Patent
Eshel et al.

(10) Patent No.: US 6,893,430 B2
(45) Date of Patent: May 17, 2005

(54) URETHRAL CATHETER AND GUIDE

(75) Inventors: Uzi Eshel, Herzlia (IL); Jacob Lazarovitz, Hod Hasharon (IL); Richard Barry Klein, Cary, NC (US)

(73) Assignee: WIT IP Corporation, Southborough, MA (US)

( * ) Notice: Subject to any disclaimer, the term of this patent is extended or adjusted under 35 U.S.C. 154(b) by 196 days.

(21) Appl. No.: 10/340,132

(22) Filed: Jan. 10, 2003

(65) Prior Publication Data

US 2003/0153899 A1 Aug. 14, 2003

Related U.S. Application Data

(60) Division of application No. 09/239,312, filed on Jan. 29, 1999, which is a continuation-in-part of application No. 09/018,664, filed on Feb. 4, 1998, now Pat. No. 5,916,195.

(51) Int. Cl.$^7$ .............................................. A61M 27/00
(52) U.S. Cl. ................... 604/544; 604/102.03
(58) Field of Search ......................... 604/96.01, 101.01, 604/102.01–102.03, 104, 164.01, 164.03–164.13, 174, 508–510, 517, 327–329, 915, 920, 540, 544

(56) References Cited

U.S. PATENT DOCUMENTS

| 2,693,191 A | 11/1954 | Raiche |
| 3,045,677 A | 7/1962 | Wallace |
| 3,625,793 A | 12/1971 | Sheridan et al. |
| 3,811,450 A | 5/1974 | Lord |
| 3,825,013 A | 7/1974 | Craven |
| 3,938,529 A | 2/1976 | Gibbons |
| 4,019,515 A | 4/1977 | Kornblum et al. |
| 4,137,922 A | 2/1979 | Leininger et al. |
| 4,183,102 A | 1/1980 | Guiset |
| 4,407,271 A | 10/1983 | Schiff |

(Continued)

FOREIGN PATENT DOCUMENTS

| DE | 19540919 | 7/1997 |
| EP | 0341988 B1 | 11/1989 |
| EP | 0733379 A1 | 9/1996 |
| EP | 0790041 A2 | 8/1997 |
| FR | 95/00869 | 6/1995 |
| WO | WO92/04934 | 2/1992 |
| WO | WO92/18199 | 10/1992 |
| WO | WO93/04727 | 3/1993 |
| WO | WO 96/02210 A1 | 6/1995 |
| WO | WO9602210 A1 | 2/1996 |

*Primary Examiner*—Nicholas D. Lucchesi
*Assistant Examiner*—Michael M Thompson
(74) *Attorney, Agent, or Firm*—Ganz Law, PC; Bradley M. Ganz; James L. Wolfe

(57) ABSTRACT

An indwelling catheter for insertion into a patient's urinary tract is provided that includes first and second tubular members that enable drainage of physiological fluids. An inflatable balloon is attached to the second tubular member. The first and second tubular members are interconnected by a connecting tube forming a gap between the first and second tubular members. The connecting tube is in fluid communication with the balloon to enable the balloon to be inflated via the connecting tube. When the balloon is anchored within the urinary bladder the second tubular member is located within the prostatic urethra with one end in close proximity to the sphincter and the other end protruding into the urinary bladder. The first tubular member is located within the penile urethra with one end in close proximity to the sphincter so that the connecting tube traverses the sphincter permitting voluntary control of the sphincter.

25 Claims, 7 Drawing Sheets

U.S. PATENT DOCUMENTS

| | | |
|---|---|---|
| 4,474,569 A | 10/1984 | Newkirk |
| 4,498,473 A | 2/1985 | Gereg |
| 4,555,242 A | 11/1985 | Saudagar |
| 4,610,660 A | 9/1986 | Rosenberg |
| 4,627,837 A | 12/1986 | Gonzalo |
| 4,655,746 A | 4/1987 | Daniels et al. |
| 4,671,795 A | 6/1987 | Mulchin |
| 4,686,985 A | 8/1987 | Lottick |
| 4,693,704 A | 9/1987 | Ogita |
| 4,710,169 A | 12/1987 | Christopher |
| 4,713,058 A | 12/1987 | Sachse |
| 4,762,129 A | 8/1988 | Bonzel |
| 4,762,130 A | 8/1988 | Fogarty et al. |
| 4,793,351 A | 12/1988 | Landman et al. |
| 4,819,751 A | 4/1989 | Shimada et al. |
| 4,823,812 A | 4/1989 | Eshel et al. |
| 4,878,901 A | 11/1989 | Sachse |
| 4,909,785 A | 3/1990 | Burton et al. |
| 4,931,037 A | 6/1990 | Wetterman |
| 4,932,938 A | 6/1990 | Goldberg et al. |
| 4,932,956 A | 6/1990 | Reddy et al. |
| 4,946,449 A | 8/1990 | Davis, Jr. |
| 4,950,227 A | 8/1990 | Savin et al. |
| 4,955,859 A | 9/1990 | Zilber |
| 4,973,301 A | 11/1990 | Nissenkorn |
| 4,979,948 A | 12/1990 | Geddes et al. |
| 4,983,167 A | 1/1991 | Sahota |
| 4,994,066 A | 2/1991 | Voss |
| 4,995,872 A | 2/1991 | Ferrara |
| 5,007,437 A | 4/1991 | Sterzer |
| 5,007,898 A | 4/1991 | Rosenbluth et al. |
| 5,019,075 A | 5/1991 | Spears et al. |
| 5,041,092 A | 8/1991 | Barwick |
| 5,059,169 A | 10/1991 | Zilber |
| 5,098,374 A | 3/1992 | Othel-Jacobsen et al. |
| 5,098,379 A | 3/1992 | Conway |
| 5,112,306 A | 5/1992 | Burton et al. |
| 5,151,100 A | 9/1992 | Abele et al. |
| 5,163,906 A | 11/1992 | Ahmadi |
| 5,176,626 A | 1/1993 | Soehendra |
| 5,188,596 A | 2/1993 | Condon et al. |
| 5,192,289 A | 3/1993 | Jessen |
| 5,269,802 A | 12/1993 | Garber |
| 5,295,959 A | 3/1994 | Gurbel et al. |
| 5,306,241 A | 4/1994 | Samples |
| 5,312,430 A | 5/1994 | Rosenbluth |
| 5,314,443 A | 5/1994 | Rudnick |
| 5,322,501 A | 6/1994 | Mahmud-Durrani |
| 5,338,302 A | 8/1994 | Hasson |
| 5,372,600 A | 12/1994 | Beyar et al. |
| 5,383,856 A | 1/1995 | Bersin |
| 5,391,196 A | 2/1995 | Devonec |
| 5,419,763 A | 5/1995 | Hildebrand |
| 5,439,446 A | 8/1995 | Barry |
| 5,451,218 A | 9/1995 | Moore |
| 5,453,090 A | 9/1995 | Martinez et al. |
| 5,478,349 A | 12/1995 | Nicholas |
| 5,484,411 A | 1/1996 | Inderbitzen et al. |
| 5,499,994 A | 3/1996 | Tihon et al. |
| 5,514,092 A | 5/1996 | Forman |
| 5,514,178 A | 5/1996 | Torchio |
| 5,518,498 A | 5/1996 | Lindenberg et al. |
| 5,527,336 A | 6/1996 | Rosenbluth |
| 5,545,132 A | 8/1996 | Fagan et al. |
| 5,549,559 A | 8/1996 | Eshel |
| 5,588,965 A | 12/1996 | Burton |
| 5,593,412 A | 1/1997 | Martinez et al. |
| 5,609,583 A | 3/1997 | Hakki et al. |
| 5,669,930 A | 9/1997 | Igarashi |
| 5,685,847 A | 11/1997 | Barry |
| 5,718,686 A | 2/1998 | Davis |
| 5,725,547 A | 3/1998 | Chuter |
| 5,752,971 A | 5/1998 | Rosenbluth |
| 5,766,209 A | 6/1998 | Devonec |
| 5,785,641 A | 7/1998 | Davis |
| 5,836,951 A | 11/1998 | Rosenbluth |
| 5,876,417 A | 3/1999 | Devonec et al. |
| 5,876,517 A | 3/1999 | Jeannier |
| 5,916,195 A | 6/1999 | Eshel et al. |

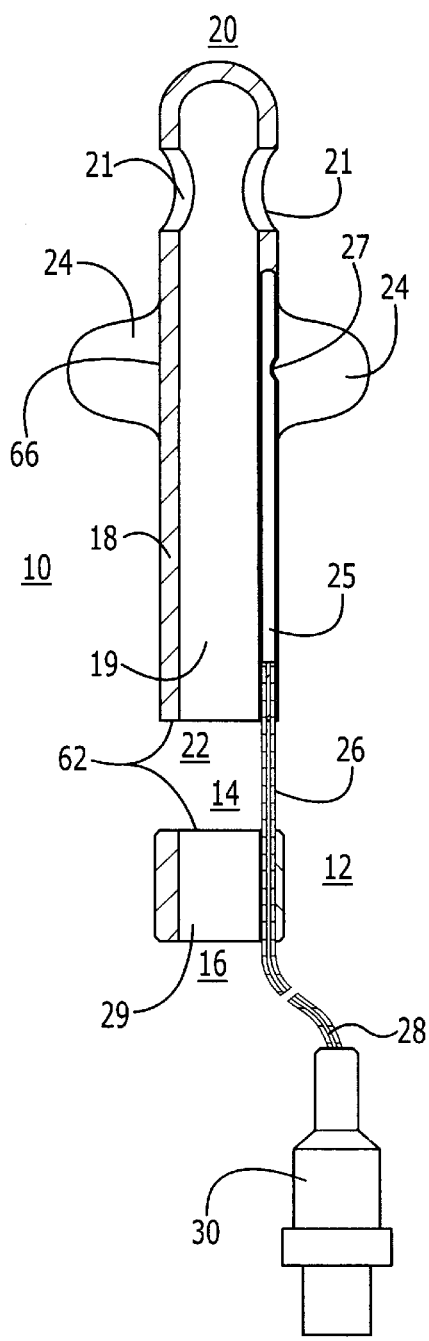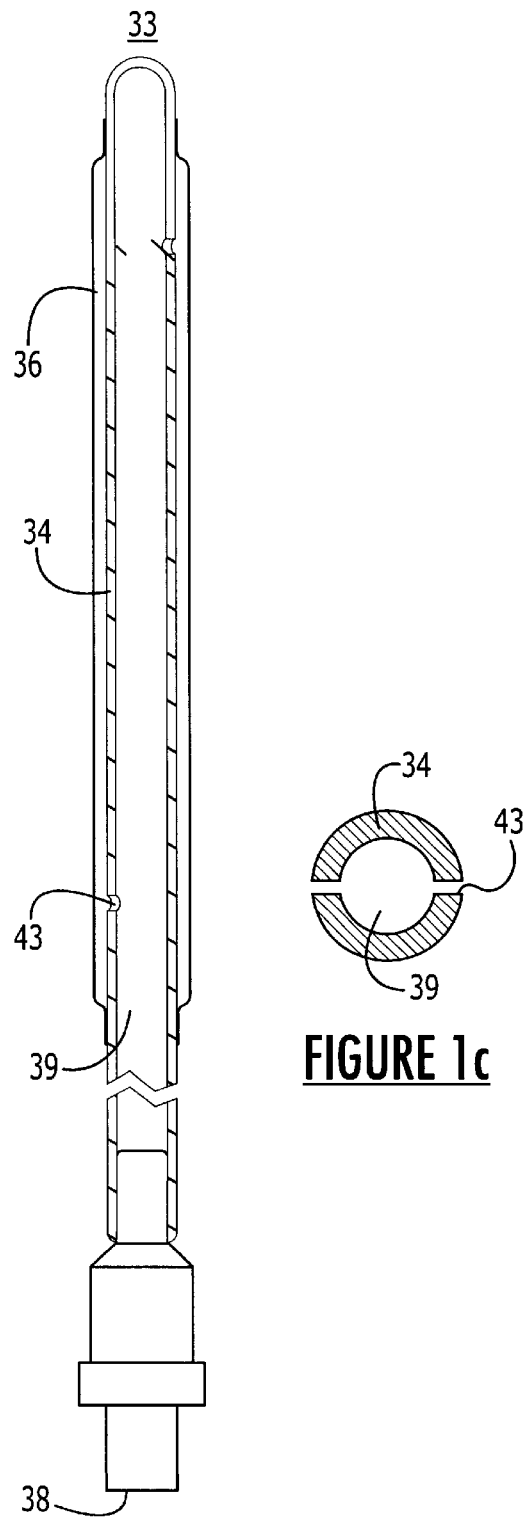
FIGURE 1a  FIGURE 1b  FIGURE 1c

URETHRAL CATHETER AND GUIDE

RELATED APPLICATIONS

This application is a divisional of U.S. patent application Ser. No. 09/239,312, filed Jan. 29, 1999, which is a continuation-in-part of U.S. patent application Ser. No. 09/018,664, filed Feb. 4, 1998, now U.S. Pat. No. 5,916,195, the contents of each being hereby incorporated by reference in their entirety as if recited in full herein.

This is a continuation-in-part of U.S. patent application Ser. No. 09/018,664, filed Feb. 4, 1998, the specification of which is hereby incorporated by reference.

FIELD AND BACKGROUND OF THE INVENTION

The present invention relates to an internal catheter for insertion into the urethra of a patient and to a catheter guide for effecting such insertion, More particularly, the present invention relates to an indwelling catheter specifically adapted for treating obstruction of the prostatic urethra and to a catheter guide, for flushing the patient's urinary tract and for the insertion and positioning of the catheter therewithin. The invention further relates to a method of inserting and positioning an indwelling catheter in the urinary tract of a patient using the guide of the present invention.

Benign prostate hyperplasia (BPH) is a condition wherein enlargement of the prostate gland constricts and blocks the portion of the urethra traversing the prostate (i.e., the prostatic urethra) and leads to difficulties in normal urination.

BPH is typically treated by using surgical procedures such as trans urethral resection of the prostate (TURP) or preferably by non-surgical procedures, such as thermal ablation of the prostate, a procedure which typically employs a catheter supplemented with a balloon head positioned within the prosthetic urethra, in which balloon heated water is recirculated.

Following a thermal ablation procedure, temporary blockage of the prostatic urethra is usually experienced due to extensive swelling and edema formation. Proper healing of the prostatic tissue and long-term urination of the patient requires the removal of the ablation balloon catheter and the subsequent insertion of a drainage catheter into the prostatic urethra.

Several types of drainage catheters are known. One type includes tubing leading from the bladder through the entire length of the urinary tract to the outside. Such catheters, beside being highly uncomfortable, suffer from two major limitations. First, such catheters do not allow voluntary urination. Second, upon prolonged installation, they frequently cause urinary tract infections.

Another type includes indwelling catheters which are typically used when long catheterizing periods are required, such as following BPH elimination treatment, during the healing of the tissues damaged by the treatment. During this time period the healing and scarring of the prostate tissue around the catheter ensures that the prostatic urethra remains dilated after the catheter is removed.

Presently, there exist various indwelling catheters for insertion into the patient's urinary tract for enabling effective drainage of fluids and tissue particles following a prostate unblocking procedure.

Examples of such indwelling catheters are disclosed in U.S. Pat. Nos. 3,811,450; 5,176,626; and 5,514,178.

An indwelling catheter employed in treating and unblocking of a prostatic urethra must meet several requirements. The catheter must have a portion which traverses the blocked prostatic urethra. The catheter must allow the patient control over urination, either biologically (voluntary sphincter control) or mechanically (e.g., a mechanical valve). In addition, an indwelling catheter must be appropriately positioned and anchored, such that no permanent movement of the device is experienced during service.

To meet the above requirements, presently employed indwelling catheters have incorporated several configurations of inflatable balloons, for anchoring and appropriately positioning the catheter within the patient's urinary tract. Such configurations typically include balloons, such as in Folley catheters, in which a positioning and anchoring balloon is positioned within the patient's bladder and is anchored against the inner-wall of the bladder opening, or ring type balloons which are inflated against the prostatic urethra and serve to both unblock the prostatic urethra and establish a tract for urination. Furthermore, balloons which are carried on the catheter itself, or alternatively on a catheter guide used for its insertion and positioning, serve for appropriately inserting and positioning the catheter by functioning as "insertion halters" and as "position reference" when halted by the patient's sphincter.

Other anchoring methods, as demonstrated by the transurethral bridge feature of the catheter produced by Boston Scientific (known as TRESTLE), a schematic depiction of which is shown in FIG. 5, also exist.

In this configuration, the placement of two tubes, interconnected by a wire, on opposite sides of the sphincter anchors the catheter against longitudinal displacement, and also allows patient voluntary control over urination.

Limitations are inherent to the catheters of the above mentioned designs. For example, some catheters are constructed such that they traverse the sphincter region of the urethra, not allowing for sphincter closure and thus necessitating the use of a valved line for urination control. These catheters are further limited in such that the urination line which leads from the bladder to the outside environment is often the cause of urinary tract infections, which necessitate the removal of the catheter, followed by antibiotic treatment and repositioning of a new catheter, causing great discomfort to the patient. On the other hand, catheters employing transurethral bridges often tend to proximally displace within the urethra when the patient urinates, due to a relief in the anchoring of the catheter upon sphincter dilation.

Additionally, positioning of a catheter via a sphincter balloon can often be difficult and time consuming, whereas positioning of a catheter via a bladder balloon often necessitates a more complex guide and catheter system.

There is thus a widely recognized need for, and it would be highly advantageous to have, an indwelling urethral catheter devoid of the above limitations. The catheter according to the present invention can be used for drainage of fluids and tissue particles through the patient's prostatic urethra following a non-surgical medical procedure such as thermal ablation of the prostate, wherein a long-term indwelling catheter is needed, while allowing voluntary control over urination.

SUMMARY OF THE INVENTION

According to one aspect of the invention described below, there is provided an indwelling catheter for insertion into a patient's urinary tract, the tract including a urinary bladder, a prostatic urethra, a sphincter and a penile urethra, the indwelling catheter comprising (a) a first tubular member having a distal end and a proximal end; (b) a second tubular member having a length, a distal end and a proximal end, the first and second tubular members having such a diameter for enabling drainage of physiological fluids therethrough; (c) a first inflatable balloon being inflatably attached at a portion of the second tubular member; and (d) a first connecting tube of substantially smaller diameter interconnecting the first and second tubular members to form a gap of a known maximal length between the first and second tubular members, the first connecting tube being in fluid communication with the first inflatable balloon, so as to enable inflating the first inflatable balloon via the first connecting tube; wherein the length of the second tubular member, the known maximal length of the gap and a location of the portion of the second tubular member to which the first inflatable balloon is inflatably attached are selected such that, when positioned in the urinary tract, the balloon is anchored within the urinary bladder, so as to position the second tubular member within the prostatic urethra with its proximal end positioned distally, and in close proximity, to the sphincter, and with its distal end protruding into the urinary bladder, and further so as to position the first tubular member within the penile urethra with its distal end positioned proximally, and close proximity, to the sphincter, while the first connecting tube traverses the sphincter, thereby permitting voluntary control of the sphincter.

According to one embodiments of the invention described below the catheter further comprises a second inflatable balloon inflatably connected to a second portion of the second tubular member and proximally to the first inflatable balloon.

According to still further features in the described preferred embodiments the second inflatable balloon of the catheter is adapted to contain a heated fluid and is therefore usable for thermal treatment (e.g., ablation) procedures.

According to still further features in the described preferred embodiments the first inflatable balloon and the second inflatable balloon of the catheter form a single notched balloon.

According to still further features in the described preferred embodiments the second inflatable balloon of the catheter is in fluid communication with the first connecting tube and thereby inflatable via the first connecting tube.

According to still further features in the described preferred embodiments the second inflatable balloon of the catheter is in fluid communication with a second connecting tube, the second connecting tube interconnecting the first and second tubular members parallely to the first connecting tube, such that inflation of the second inflatable balloon is effected independently of the inflation of the first inflatable balloon.

According to further features in the described preferred embodiments of the present invention the catheter further comprises a detachable guiding element, the guiding element including an elongated tubular member, an elongated inflatable balloon being attached to at- least a portion of the length of the elongated tubular member, and a first mechanism for inflating the elongated inflatable balloon. The guiding element being dimensioned for insertion through the first and second tubular members, such that when the elongated inflatable balloon is inflated the catheter is fixed to the guiding element.

According to further features in the described preferred embodiments of the present invention the elongated tubular member of the guiding element is formed with a distal opening, the guiding element further includes a second mechanism for conducting a fluid through the elongated tubular member.

According to further features in the described preferred embodiments of the present invention the elongated tubular member of the guiding element is formed with a closed distal end and further wherein a cavity of the elongated tubular member is in fluid communication with the elongated inflatable balloon via at least one opening.

According to still further features in the described preferred embodiments the guiding element further includes a second inflatable balloon attached to a portion of the elongated tubular member distally to the elongated inflatable balloon and a second mechanism for inflating the second balloon.

According to another aspect of the present invention there is provided an indwelling catheter for insertion into a patient's urinary tract comprising (a) a first tubular member having a distal end and a proximal end; (b) a second tubular member having a length, a distal end and a proximal end, the first and second tubular members having such a diameter for enabling drainage of physiological fluids therethrough; (c) a first inflatable balloon being inflatably attached at a portion of the second tubular member; (d) a first connecting tube of substantially smaller diameter interconnecting the first and second tubular members to form a gap of a known maximal length between the first and second tubular members, the first connecting tube being in fluid communication with the first inflatable balloon, so as to enable inflating the first inflatable balloon via the first connecting tube; and (e) a second inflatable balloon inflatably connected to a second portion of the second tubular member and proximally to the first inflatable balloon.

According to another aspect of the present invention there is provided a guiding element for guiding a catheter comprising an elongated tubular member, a first and elongated inflatable balloon being attached to at least a portion of the length of the elongated tubular member, and a first mechanism for inflating the elongated inflatable balloon. A second inflatable balloon, is provided, attached to a portion of the elongated tubular member distally to the elongated inflatable balloon, and a second mechanism for inflating the second balloon. The guiding element being dimensioned for insertion through the catheter, such that when the elongated inflatable balloon is inflated the catheter is fixed to the guiding element.

According to another aspect of the present invention there is provided a method of positioning an indwelling catheter in a patient's urinary tract, the tract including a urinary bladder, a prostatic urethra, a sphincter and a penile urethra, the method comprising the steps of (a) providing an indwelling catheter including (i) a first tubular member having a distal end and a proximal end; (ii) a second tubular member having a length, a distal end and a proximal end, the first and second tubular members having such a diameter for enabling drainage of physiological fluids therethrough; (iii) a first inflatable balloon being inflatably attached at a portion of the second tubular member; and (iv) a first connecting tube of substantially smaller diameter interconnecting the first and second tubular members to form a gap of a known maximal length between the first and second tubular members, the first connecting tube being in fluid communication with the first inflatable balloon, so as to enable inflating the first inflatable balloon via the first connecting tube; (b) attaching the indwelling catheter to a guiding element; and (c) inserting the indwelling catheter via the guiding element into the patient's urinary tract and positioning the indwelling catheter therein such that the first tubular member engages a portion of the penile urethra proximally to the sphincter, the second tubular member engages the prostatic urethra distally to the sphincter and having its distal end protruding into the urinary bladder, the connecting tube traverses the sphincter.

According to a preferred embodiment positioning the indwelling catheter in the patient's urinary tract is effected by inserting the first inflatable balloon into the urinary bladder, inflating the first inflatable balloon and via the connecting tube pulling the catheter, so as to position the inflatable balloon against a wall of the urinary bladder.

According to another preferred embodiment the method of positioning the indwelling catheter in a patient's urinary tract, further comprises the step of removing the guiding element.

According to another embodiment the method of positioning an indwelling catheter in a patient's urinary tract further comprises the step of deflating the first inflatable balloon.

According to another aspect of the present invention there is provide a method of positioning an indwelling catheter in a patient's urinary tract, the tract including a urinary bladder, a prostatic urethra, a sphincter and a penile urethra, the method comprising the steps of (a) providing an indwelling catheter including (i) a first tubular member having a distal end and a proximal end; (ii) a second tubular member having a length, a distal end and a proximal end, the first and second tubular members having such a diameter for enabling drainage of physiological fluids therethrough; (iii) a connecting element of substantially smaller diameter interconnecting the first and second tubular members to form a gap of a known maximal length between the first and second tubular members; (b) attaching the indwelling catheter to a guiding element, the guiding element including an inflatable balloon attached thereto; and (c) inserting the indwelling catheter via the guiding element into the patient's urinary tract and positioning the indwelling catheter therein such that the first tubular member engages a portion of the penile urethrproximally to the sphincter, the second tubular member engages the prostatic urethra distally to the sphincter and having its distal end protruding into the urinary bladder, the connecting element traverses the sphincter.

According to a preferred embodiment of the present invention the inflatable balloon of the elongated tubular member is positioned at a portion of the guiding element, such that when the guiding element engages the indwelling catheter, the inflatable balloon is inflatably positioned distally to the catheter, whereas positioning the indwelling catheter is effected by inserting the inflatable balloon into the urinary bladder, inflating the inflatable balloon and pulling the guiding element so as to position the inflatable balloon against a wall of the bladder.

According to another aspect of the present invention there is provided a method of urinating a patient following a prostate ablation procedure, the patient's urinary tract including a urinary bladder, a prostatic urethra, a sphincter and a penile urethra the, the method comprising the steps of (a) providing an indwelling catheter including (i) a first tubular member having a distal end and a proximal end; (ii) a second tubular member having a length, a distal end and a proximal end, the first and second tubular members having such a diameter for enabling drainage of physiological fluids therethrough; (iii) an inflatable balloon being inflatably attached at a portion of the second tubular member; (iv) a connecting tube of substantially smaller diameter interconnecting the first and second tubular members to form a gap of a known maximal length between the first and second tubular members, the first connecting tube being in fluid communication with the first inflatable balloon, so as to enable inflating the first inflatable balloon via the first connecting tube; (b) attaching the indwelling catheter to a guiding element; (c) inserting the indwelling catheter via the guiding element into the patient's urinary tract and positioning the indwelling catheter therein such that the first tubular member engages a portion of the penile urethra proximally to the sphincter, the second tubular member engages the prostatic urethra distally to the sphincter and having its distal end protruding into the urinary bladder, the connecting tube traverses the sphincter, and (d) removing the guiding element.

According to another aspect of the present invention there is provided a method of dilating a prostatic urethra of a patient following a prostate ablation procedure, while at the same time urinating the patient, the method comprising the steps of (a) inserting a drainage catheter into a urinary tract of the patient, the catheter including an inflatable balloon; (b) positioning the catheter within the urinary tract such that the inflatable balloon engages the prostatic urethra; and (c) inflating the inflatable balloon, so as to dilate the prostatic urethra.

According to an embodiment of the present invention the method of dilating a prostatic urethra, further comprises the steps of deflating said inflatable balloon and removing said drainage catheter.

According to another aspect of the present invention there is provided a method of ablating a prostatic urethra of a patient during a prostate ablation procedure, while at the same time implanting a drainage catheter in a urinary tract of the patient for urinating the patient following the ablation procedure, the method comprising the steps of (a) inserting an ablating-drainage catheter into a urinary tract of the patient, the catheter including an inflatable balloon; (b) positioning the catheter within the urinary tract such that the inflatable balloon engages the prostatic urethra; (c) inflating the inflatable balloon with a heated fluid so as to ablate the prostatic urethra; and (d) leaving the ablating-drainage catheter in the urinary tract for urinating the patient following the ablation procedure.

According to a preferred embodiment of the present invention, the inflatable balloon of the catheter is maintained inflated for dilating the prostatic urethra following the ablation procedure.

According to an embodiment of the present invention the method of ablating a prostatic urethra and at the same time urinating a patient further comprises the steps of removing the ablating-drainage catheter.

Further according to an embodiment of the present invention, there is provided an indwelling catheter for insertion into a patient's urinary tract, the tract including a urinary bladder, a prostatic urethra, a sphincter and a penile urethra, the indwelling catheter comprising (a) a first tubular member having a distal end and a proximal end; (b) a second tubular member having a length, a distal end and a proximal end, the first and second tubular members having such a diameter for enabling drainage of physiological fluids therethrough; (c) a first inflatable balloon inflatably connected to a portion of the second tubular member; and (d) a first connecting tube of substantially smaller diameter interconnecting the first and second tubular members to form a gap of a known maximal length between the first and second tubular members, the first connecting tube being in fluid communication with the first inflatable balloon, so as to enable inflating the first inflatable balloon via the first connecting tube, wherein the length of the second tubular member, the known maximal length of the gap and a location of the portion of the second tubular member to which the first inflatable balloon is inflatably attached are selected such that, when positioned in the urinary tract, the balloon engages the prostatic urethra and the second tubular member has its proximal end positioned distally, and in close proximity, to the sphincter, and its distal end protruding into the urinary bladder, whereas the first tubular member engages the penile urethra having its distal end positioned proximally, and is in close proximity, to the sphincter, while the first connecting tube traverses the sphincter, thereby permitting voluntary control of the sphincter.

Preferably, the catheter of further comprising (e) a detachable guiding element, the guiding element including (i) an elongated tubular member; (ii) an elongated inflatable balloon being attached to at least a portion of the length of the elongated tubular member; (iii) a first mechanism for inflating the elongated inflatable balloon, the guiding element being dimensioned for insertion through the first and second tubular members, such that when the elongated inflatable balloon is inflated the catheter is fixed to the guiding element; and (iv) a second inflatable balloon attached to a portion of the elongated tubular member distally to the elongated inflatable balloon and a second mechanism for inflating the second balloon, wherein the second inflatable balloon serves for positioning the catheter in the urinary tract of the patient.

The present invention successfully addresses the shortcomings of the presently known configurations by providing a catheter and guide system with simple means for accurately positioning and securely anchoring the catheter within a patient's urinary tract, such that voluntary biological control of urination is maintained. Furthermore, the catheter of the present invention can also be used to both ablate and dilate a patients prostatic urethra, while at the same time allowing the urination of the patient.

BRIEF DESCRIPTION OF THE DRAWINGS

The invention herein described, by way of example only, with reference to the accompanying drawings, wherein:

FIG. 1a is a longitudinal cross sectional view of a catheter including a positioning and anchoring inflatable balloon according to the present invention;

FIG. 1b is a longitudinal cross sectional view of a guiding element including an elongated inflatable balloon according to the present invention;

FIG. 1c is a cross sectional view of an elongated tubular element of the guiding element shown in FIG. 1b;

FIG. 4a is a longitudinal cross sectional view of a prior art catheter attached to a guiding element including two inflatable balloons according to the present invention;

FIG. 4b is a cross sectional view along line A—A in FIG. 4a;

DESCRIPTION OF THE PREFERRED EMBODIMENTS

Figures 1D, 1E:
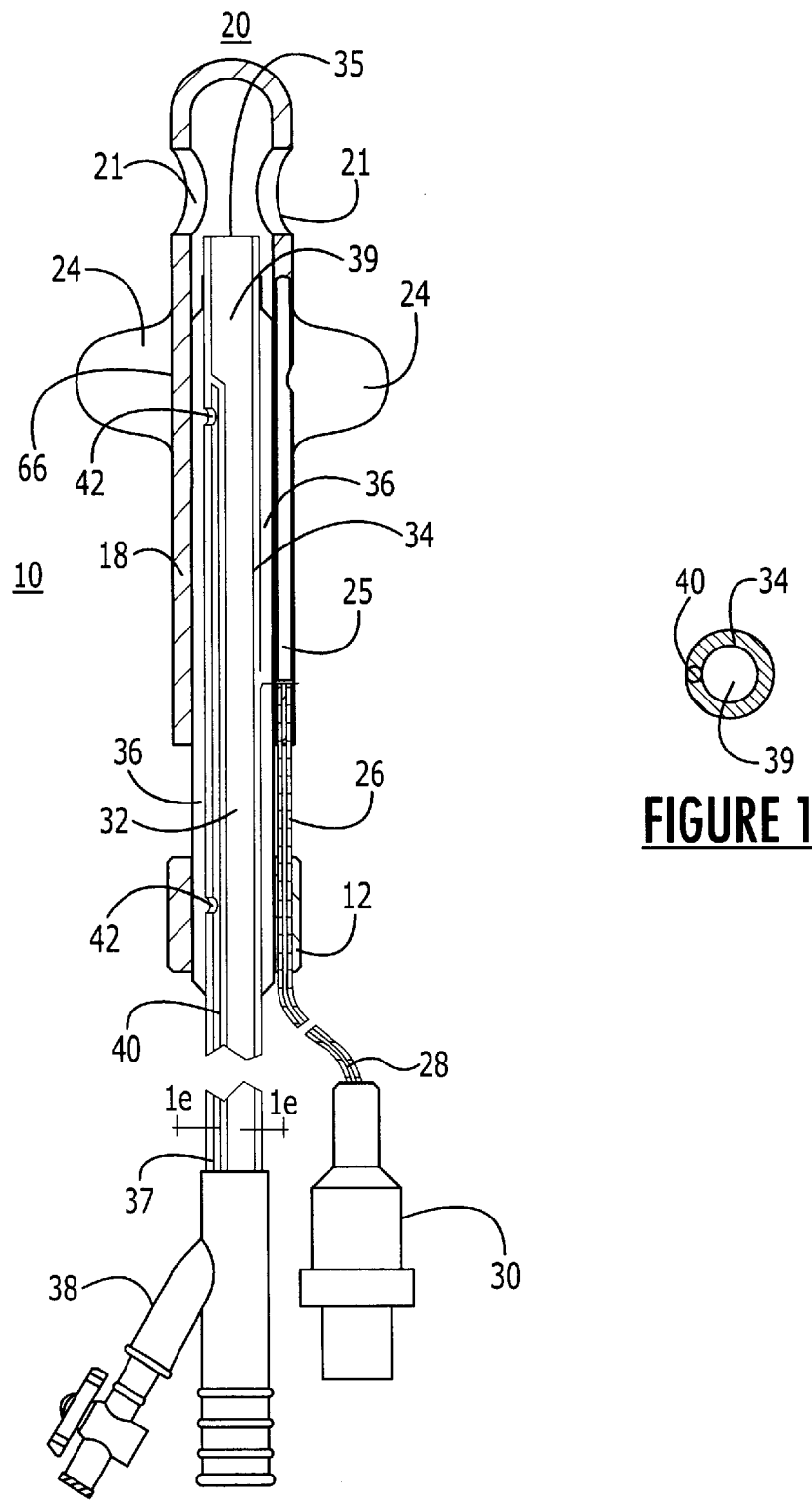
FIG. 1d is a longitudinal cross sectional view of the catheter shown in FIG. 1a and a guiding element including an elongated inflatable balloon attached thereto according to the present invention.
FIG. 1e is a cross sectional view of an elongated tubular element of the guiding element of FIG. 1d.

The present invention is of an indwelling urethral catheter which can be used for urinating a patient after a surgical procedure such as TURP or a non-surgical procedure such as thermal ablation of the prostatic urethra. Specifically the catheter of the present invention can be used for both thermal ablation and subsequent urination of the patient. The present invention is further of a catheter guiding element and catheter insertion and positioning methods to be used along with the catheter of the present invention.

The principles and operation of an indwelling urethral catheter, guiding element and methods according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

As used herein in the specification and in the claims section that follows, and in relation to the urinary tract positioning of the catheter or guiding element according to the present invention, the terms "distal" and "distally" denote towards the urinary bladder and the terms "proximal" and "proximally" denote towards the penile urethra.

Referring now to the drawings, FIGS. 1a, 1d, 2a–b, 3a–b and 6 illustrate an indwelling urethral catheter according to some preferred embodiments of the present invention, which is referred to hereinunder as catheter 10. As further detailed hereinunder, catheter 10 is designed for insertion into a patient's urinary tract and serves primarily for urinating the patient.

Catheter 10 includes a first tubular member 12 having an inner lumen 29. Member 12 has a distal open end 14 and a proximal open end 16. When catheter 10 is implanted in the patient's urinary tract, member 12 is designed to engage the distal portion of the patient's penile urethra, just proximally to the sphincter.

Catheter 10 further includes a second tubular member 18 having an inner lumen 19. Member 18 has a distal end 20 and an open proximal end 22. Distal end 20 is either open or formed with at least one opening 21. A distal portion of tubular member 18, which includes end 20 and opening 21, can feature any one of a variety of patterns known in the art and which serve for facilitating guidance of, and/or urination through, catheter 10, such as, but not limited to, Tiemann pattern (see FIG. 6, at 60), Couvelaire pattern, Dufour pattern, Mercier pattern, a whistle tip pattern and a cylindrical pattern. These patterns are further described in an endouroloay catalog by RUSCH Incorporated of 2450 Meadowbrook Parkway Duluth, Ga. 30136, and in http://www.ruesch.de, the web site thereof.

When catheter 10 is implanted, member 18 engages the prostatic urethra, having its proximal end 22 positioned just distally to the distal end of the sphincter and its distal end 20, as well as opening 21, within the bladder of the patient.

Thus, members 12 and 18 serve for draining the bladder under the voluntary control of the sphincter, which is not engaged or traversed by neither member 12 nor member 18. To this end, fluids from the bladder are directed via member 18 to the sphincter, and when the sphincter muscle is contracted, and as a result the sphincter is dilated, these fluids pass therethrough to member 12 and then discarded through the proximal end of the penile urethra.

Second tubular member 18 is preferably designed with several lengths, preferably between 2 and 14 centimeters, more preferably, between 3 and 12 centimeters, most preferably between 4 and 10 centimeters, so as to fit prostatic urethras of different patients preferably between 2 and 6 cm in length. While restrictions are imposed on the length of member 18, which should engage the entire length of the prostatic urethra and protrude into the bladder, no such length restrictions are imposed on member 12, which is shown in the drawings to be shorter than member 18, yet in reality can be substantially longer. The length of member 12 can range from about one centimeter or less to about 8–10 centimeters or more.

The inner diameter of members 12 and 18 is selected wide enough so as to enable free passage of body fluids therethrough. Inner diameters above about 5 millimeters are preferred. The outer diameter of members 12 and 18 is preferably about 6–9 millimeters. Members 12 and 18 are typically made of a resilient and hypoallergenic polymeric material, such as, but not limited to, polyethylene, polypropylene, polyurethane, polyvinyl chloride (PVC) and silicon.

First 12 and second 18 tubular members are interconnected therebetween by a connecting tube 26. Tube 26 typically serves three functions, one of which is to form a gap 62 of a known (limited) maximal length between members 12 and 18. The other functions of tube 26 are further addressed hereinunder. When catheter 10 is positioned within the urinary tract of the patient, tube 26 traverses the sphincter. The length of gap 62 is selected so as to enable the sphincter to be free of any portions of members 12 and 18. Tube 26 is of a substantially smaller diameter as compared with the diameters of members 12 and 18 (both internal and external). Tube's 26 external diameter is selected such that it does not interfere with the hermetic closure of the sphincter, and as such, allows the patient voluntary control over urination via the sphincter. Furthermore, retaining catheter 10 in position is generally achieved by the sphincter which prevents the longitudinal dislocation of members 12 and 18 when closed.

Connecting tube 26 extends through member 12 and has sufficient length so as to extend the length of the urethra, through the penis and have its proximal end outside the body of the patient. According to a preferred embodiment, the portion of connecting tube 26 that traverses member 12 is engaged within the wall of member 12. In fact, according to one embodiment, that portion of tube 26 is directly formed by a channel present in the wall of member 12.

The above described configuration is common to all of the embodiments of catheter 10 according to the present invention as further detailed hereinunder.

According to a preferred embodiment of the present invention, catheter 10 further includes an inflatable balloon 24, which is shown inflated in the drawings. Inflatable balloon 24 is attached at a portion 66 of second tubular member 18 and is positioned proximally to distal end 20 and opening 21.

Balloon 24 serves for positioning catheter 10 in the patient's urinary tract. To this end, inflatable balloon 24 is inserted in its deflated form into the patients bladder. It is thereafter inflated so as to anchor catheter 10 in place. To this end, when inflated, balloon 24 is of substantial girth, such that it forms a steepled donut shape, substantially perpendicular to, and surrounding, second tubular member 18. When inflated, inflatable balloon 24 is larger in diameter than the opening of the patient's bladder, such that subsequent pulling of catheter 10 in a proximal direction via, for example, proximal end 28 of connecting tube 26, anchors balloon 24 against the bladder's inner wall and positions first 12 and second 18 tubular members and connecting tube 26 as described hereinabove to allow voluntary control over urination.

Retaining catheter 10 in position is generally achieved by the sphincter which prevents the longitudinal dislocation of members 12 and 18 when closed. However, a possibility exists, in which, members 12 and 18 will dislocate while the sphincter is dilated (i.e., during voluntary urination). To prevent such undesired dislocation, balloon 24 is preferably retained in its inflated form also during service.

Figure 5:
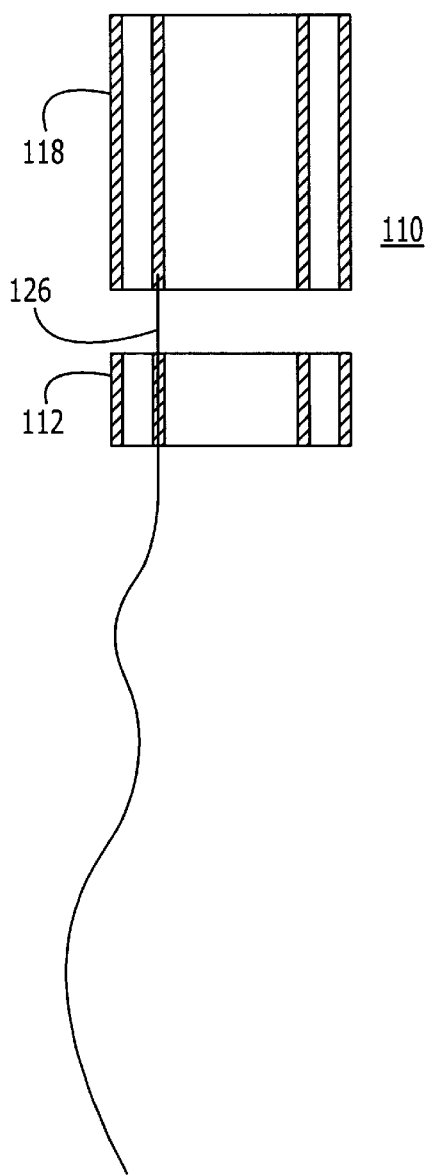
FIG. 5 is a longitudinal cross sectional view of a catheter according to the prior art.
Figure 6:
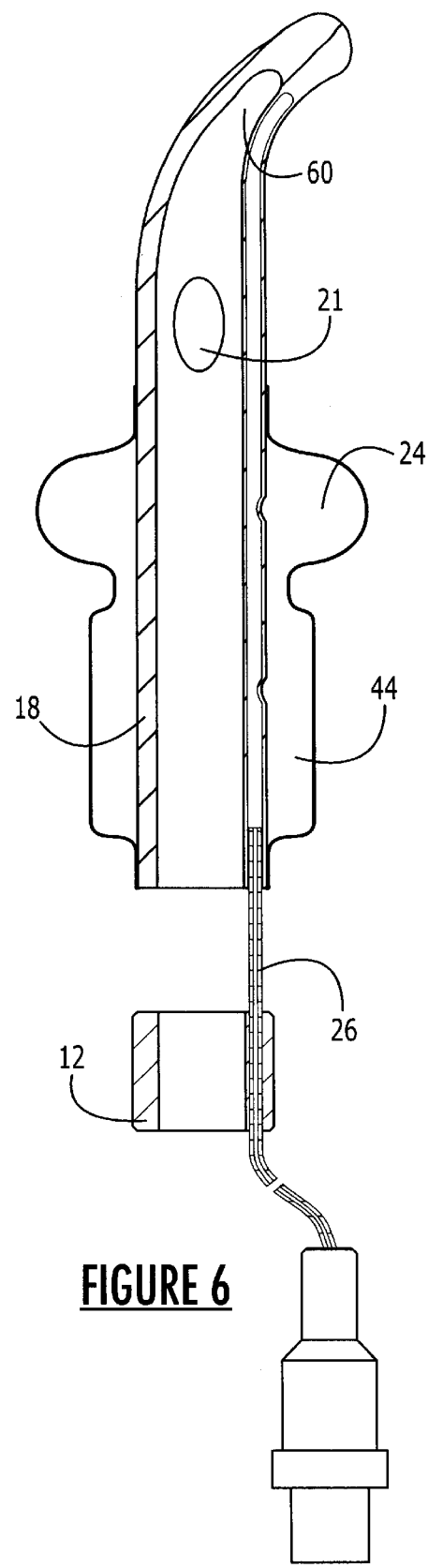
FIG. 6 is a longitudinal cross sectional view of a catheter according to the present invention, which includes two integrated inflatable balloons and which is supplemented with a Tiemann pattern tip.

It will be appreciated that the prior art catheter of Boston Scientific, which is described in the Background section hereinabove and is shown in FIG. 5, can dislocate when the patient urinates, due to dilation of the sphincter during urination.

Thus, catheter 10 of the present invention provides a second and effective means, unaffected by urination of the patient, for retaining catheter 10 appropriately positioned in the urinary tract.

An additional function attributed to connecting tube 26 involves the inflation/deflation of balloon 24. To this end, connecting tube 26 traverses a distal portion of member 18. The portion of connecting tube that traverses the distal portion of member 18 is preferably engaged within the wall of member 18. In fact, according to one embodiment, that portion of tube 26 is formed by a channel 25 present in the wall of member 18. Thus, tube 26 can be formed by tubular portions in part, and channels in part.

According to the present invention, tube 26 is in fluid communication with inflatable balloon 24. The fluid communication between tube 26 and balloon 24 is formed either by directly connecting a tubular portion of tube 26 to balloon 24, or preferably by an opening 27 formed in the wall of member 18 forming a fluid communication between channel 25 and balloon 24. Thus, a direct fluid passage exists between tube 26 and balloon 24.

An adapter 30 is preferably connected at proximal end 28 of tube 26, to enable the connection of an inflation device, such as, but not limited to, a syringe or a pump, thereto, so as to enable inflation and/or deflation of inflatable balloon 24. Deflation of balloon 24 can also be performed passively. Preferably inflation and/or deflation of balloon 24 is achieved with air but other fluids, such as water, can also be used, as well as other gasses, such as nitrogen.

According to another preferred embodiment of the present invention, and as specifically shown in FIGS. 2a–b and 3a–b, catheter 10 further or alternatively includes an additional inflatable balloon 44, which is shown inflated in the drawings. Balloon 44 is inflatably connected to a second portion 68 of second tubular member 18 and proximally to balloon 24, in cases the latter is present.

When catheter 10 is appropriately positioned within the urinary tract of the patient, balloon 44 is designed to engage the prostatic urethra. Balloon 44 can serve several functions, as further delineated in detail below, including anchorage of catheter 10, facilitated removal of catheter 10, dilation of the prostatic urethra, ablation of the prostatic urethra and/or drug delivery thereto. To this end, when inflated, balloon 44 is more elongated, and narrower as is compared to balloon 24.

Thus, typically, balloon 44 is inflated following the positioning of catheter 10 and is utilized for the dilation of the prostatic urethra following a non surgical prostatic procedure such as, but not limited to, thermal ablation thereof. Inflated balloon 44 is retained in its inflated form until the prostatic urethra retains a dilated diameter due to scarring of tissue surrounding inflated balloon 44, at which time, and prior to the removal of catheter 10, balloon 44 is deflated.

It will be appreciated that, balloon 44 of catheter 10 can be used for thermal ablation of a prostatic urethra. In this case, catheter 10 serves both as a thermal ablation catheter and then also as a drainage catheter, without the need of catheter replacement. To this end, balloon 44 and additional components of catheter 10 are constructed from heat resistant materials, such that a heated fluid can be conducted therethrough. Preferred materials will withstand temperatures of between 55° C. to 80° C., examples include, but not limited to, PVC, silicon and polyurethane.

Following the thermal ablation procedure, balloon 44 is maintained inflated for dilation of the prostatic urethra as further described hereinabove. Thus, the present invention makes possible the use of a single device for both the thermal ablation and urination of the patient. U.S. Pat. Nos. 5,257,977; 5,549,559; and 5,492,529, which are incorporated by reference as if fully set forth herein, provide further details relating to ablation catheters directed at ablating a prosthetic urethra.

Yet, it will be appreciated that balloon 44 of catheter 10 can also serve for the diffusional release of a medicament such as, but not limited to, non-steroidal anti-inflammatory drugs typically used in post thermal ablation treatments. In this embodiment of the present invention balloon 44 is manufactured permeable to the medicament or medicaments of choice, such that a liquid carrying the medicament(s), dissolved or in suspension, can be conducted to balloon 44 and delivered to the body of the patient therethrough. Balloon 44 can be inflated with the medicament containing fluid such that it contacts the ablated prostatic urethral, and thus diffusional drug transfer is facilitated. U.S. Pat. Nos. 5,282,785; and 5,800,392, which are incorporated by reference as if fully set forth herein, provide further details relating to balloon catheter based drug delivery.

Figure 2A:
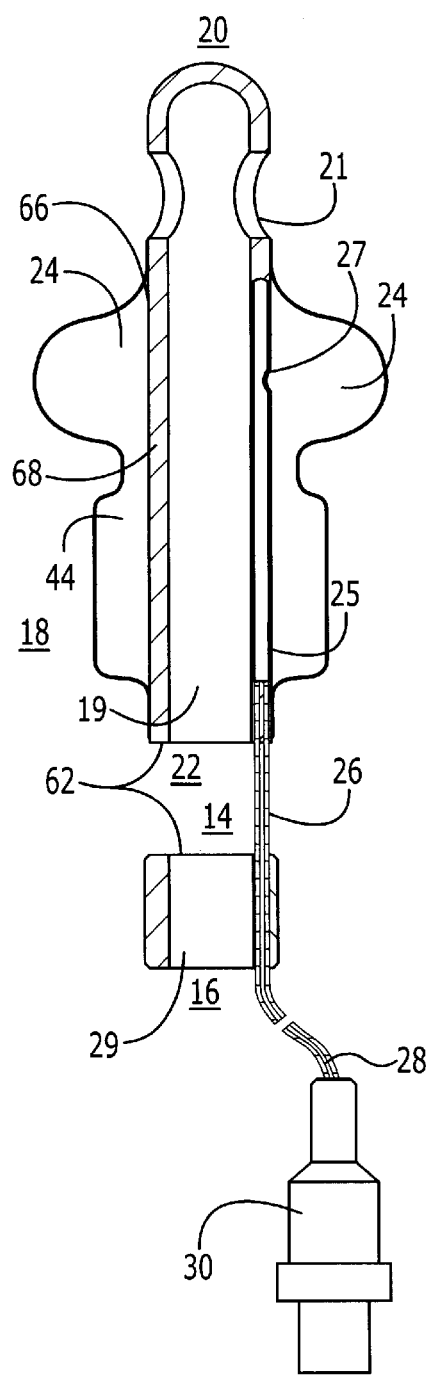
FIG. 2a is a longitudinal cross sectional view of a catheter according to another aspect of the present invention which includes two integrated inflatable balloons.
Figure 2B:
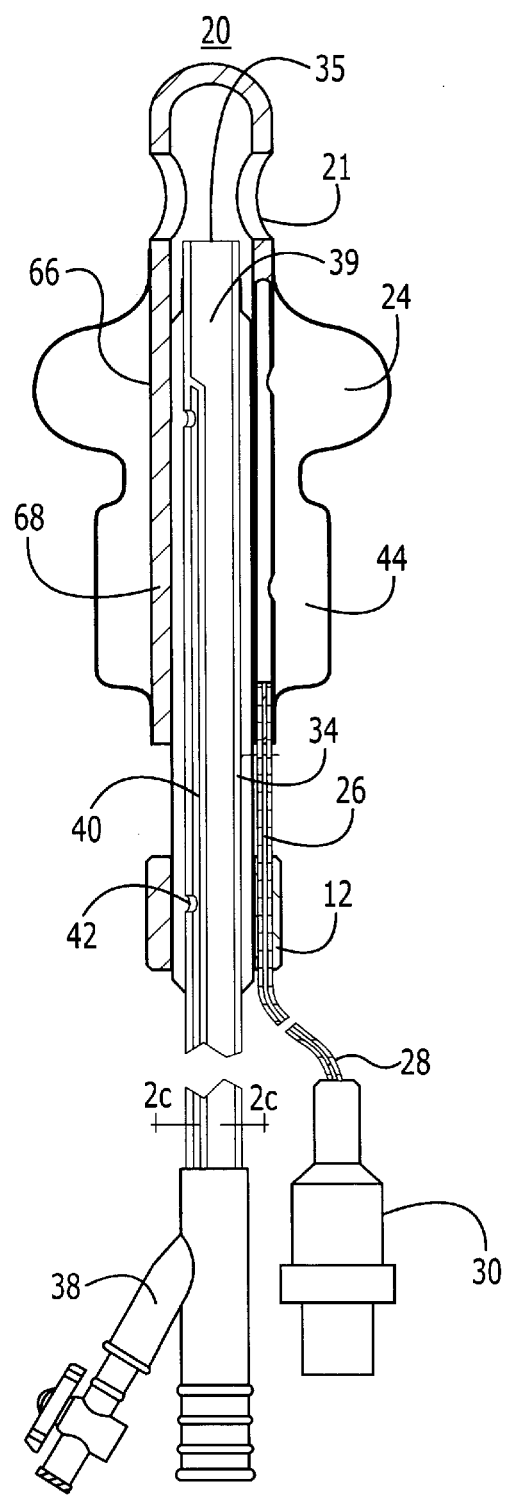
FIG. 2b is a longitudinal cross sectional view of the catheter of FIG. 2a and a guiding element attached thereto according to the present invention.
Figures 2C, 3A:
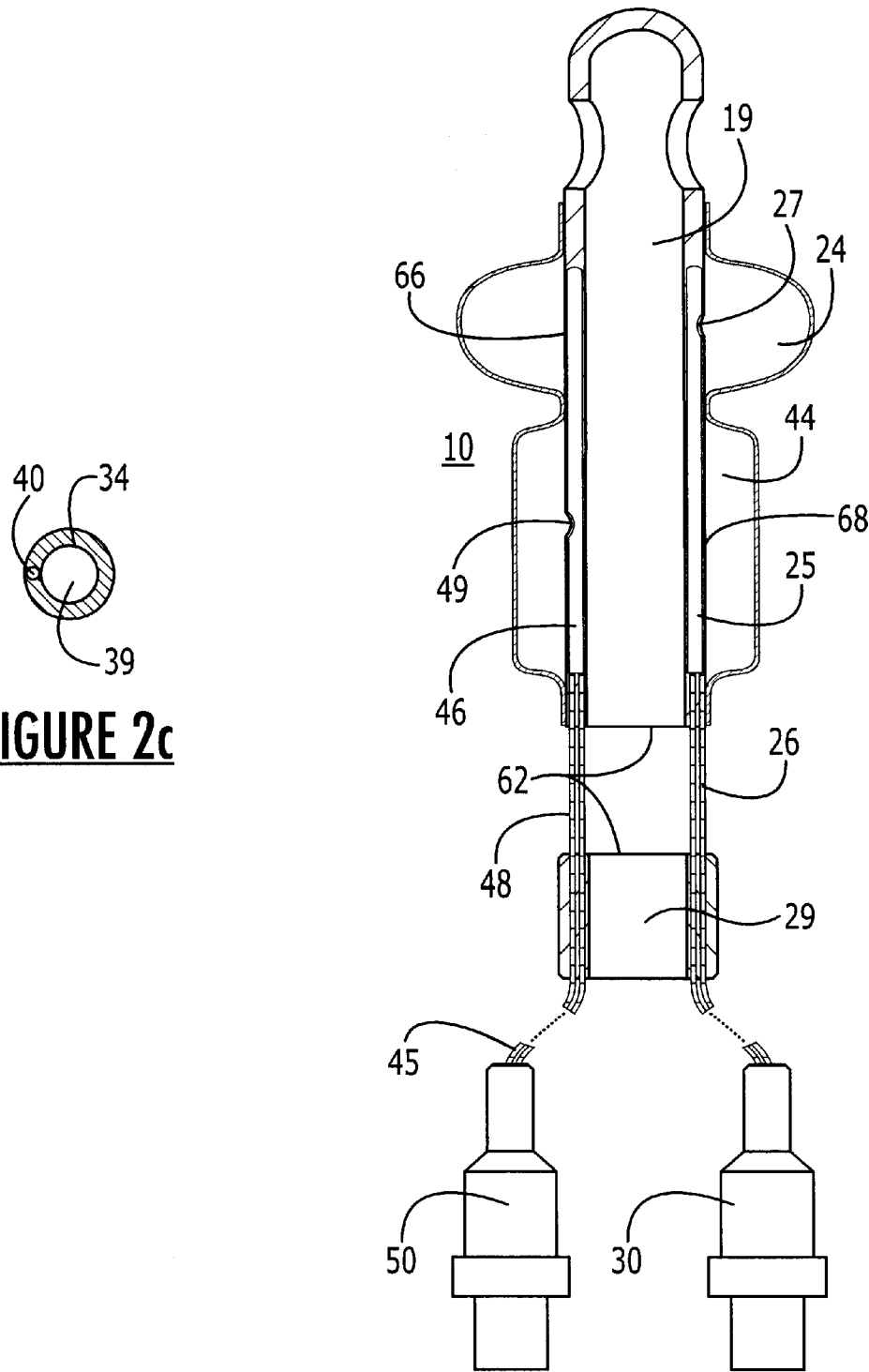
FIG. 3a is a longitudinal cross sectional view of a catheter according to yet another embodiment of the present invention, which includes two separated inflatable balloons.
Figure 3B:
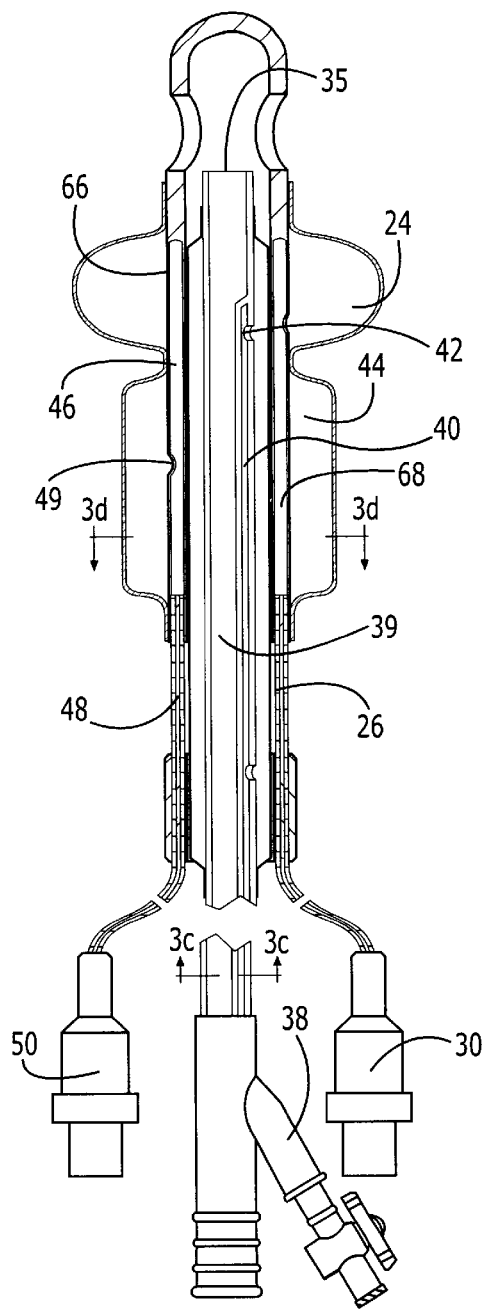
FIG. 3b is a longitudinal cross sectional view of the catheter and of FIG. 3a and a guiding element attached thereto according to the present invention.
Figure 3C:
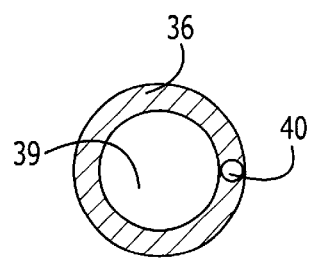
FIG. 3c is a cross sectional view along line A—A in FIG. 3b.
Figure 3D:
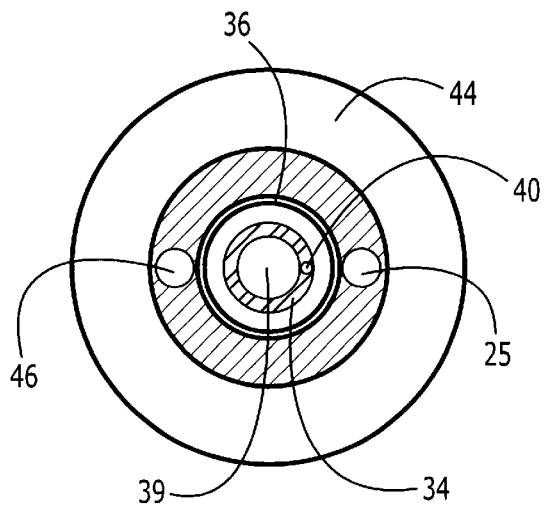
FIG. 3d is a cross sectional view along line B—B in FIG. 3b.

According to one configuration of the present invention, each of balloons 24 and 44 is independently inflated (FIGS. 3a–b). To this end an additional connecting tube 48, which substantially parallels connecting tube 26, is employed, and is provided in fluid communication with balloon 44. Connecting tube 48 establishes fluid communication with an adapter 50, provided at a proximal end 45 thereof and which is located outside the patient's body, through channel 46 formed in tubular member 18. Channel 46 is in fluid communication with balloon 44 through at least one opening 49. Inflation and deflation of balloon 44 is achieved, according to this configuration, via an inflating/deflating device, such as, but not limited to, a syringe or a pump connectable to adapter 50.

However, according to another configuration of the present invention, balloons 24 and 44 are co-inflatable. This is achieved either by forming a fluid communication between balloon 44 and tube 26 (FIGS. 2a–b) and/or by integrating balloons 24 and 44 into preferably a single notched balloon (FIGS. 2a–b), although other non-isometric shapes are also envisaged for such a balloon. In each of these cases, the degree to which each of balloons 24 and/or 44 inflates under predetermined pressure, is dictated by its specific characteristics. Typically balloon 24 is selected the first to substantially inflate, so as to serve in the process positioning catheter 10 as described above.

Guiding and positioning catheter 10 as herein described is effected according to preferred embodiments of the present invention via a guiding element, which is shown in FIGS. 1b–d, 2b–c, 3b–d and 4a at 32.

Guiding element 32 includes an elongated tubular member 34 which includes a lumen 39, and which is formed with a closed (FIG. 1b) or opened (FIGS. 1d, 2b and 3b) distal end 33 and an preferably an open proximal end 37. Guiding element 32 further includes an elongated inflatable balloon 36 inflatably attached to member 34. Balloon 36 is inflatable either via openings 43 formed in the wall of member 34 connecting lumen 39 thereof with balloon 36 (FIG. 1b), or by a dedicated channel 40 (FIGS. 1d, 2b–c and 3b–d) formed in the wall of member 34 and opens to balloon 36. A double headed adapter 38 is preferably provided in fluid communication with either lumen 39 and/or channel 40 and is used for connecting an inflating device for inflating/deflating balloon 36 and/or connecting a perfusing device for perfusing liquids in an out of the body of the patient.

The diameter of guiding element 32 is selected so as to enable its insertion through members 12 and 18 of catheter 10 when balloon 36 is deflated. Inflating balloon 36 ensures fixation of element 32 and catheter 10, such that via element 32, which is constructed of sufficient length and rigidity, catheter 10 is guided to its appropriate position within the urinary tract of the patient, as further detailed hereinabove.

Figures 4A, 4B:
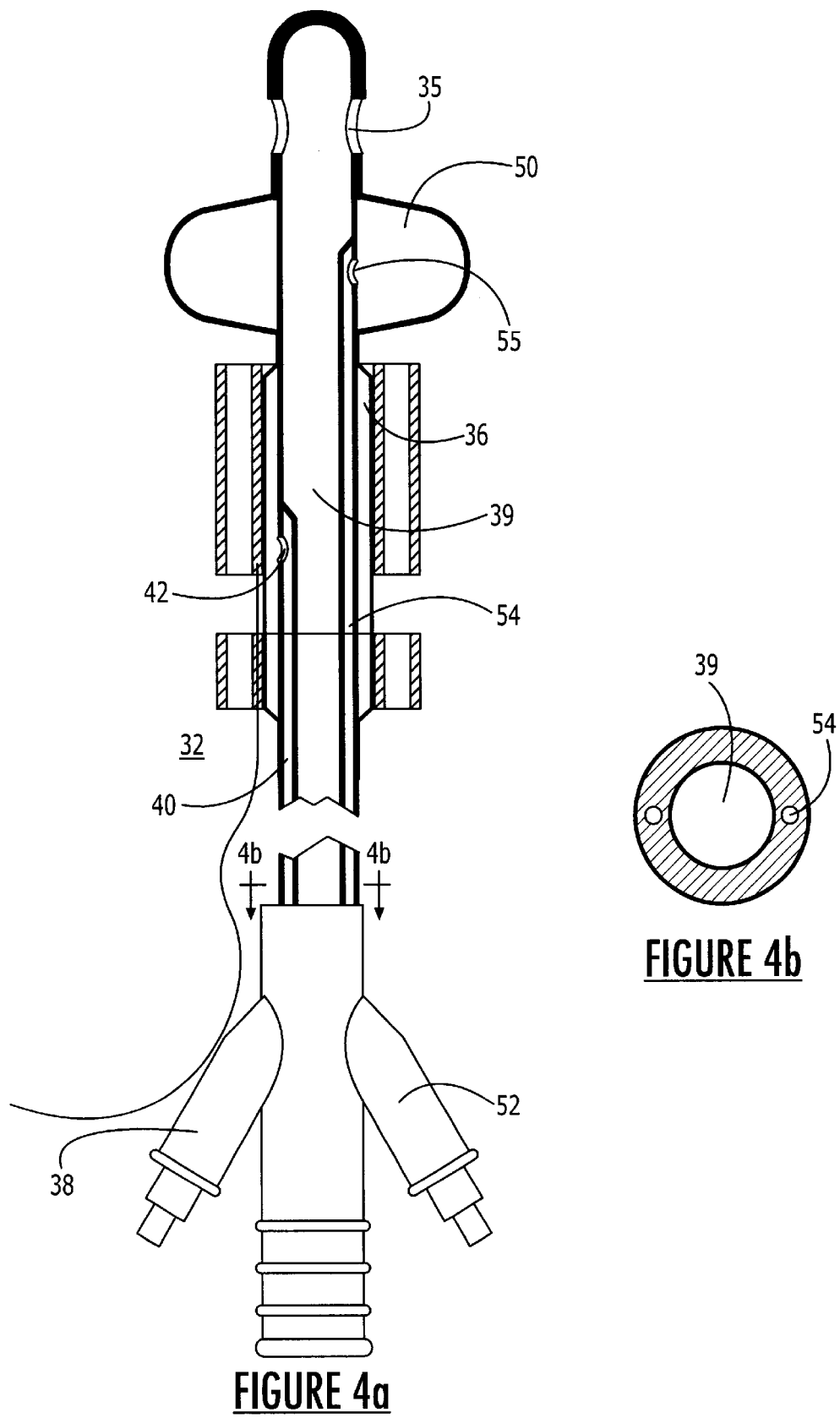

As shown in FIG. 4a, according to one embodiment of the present invention, guiding element 32 further includes an additional or alternative balloon 50, located distally to balloon 36, if the latter is present. Balloon 50 is shaped and functions similarly to balloon 24 of catheter 10. This configuration of element 32 is directed at insertion and positioning of catheters lacking a bladder positioning balloon (e.g., balloon 24). Such catheters include the configuration of catheter 10 according to the present invention in which only balloon 44 is employed, or prior art configurations in which no balloons are employed altogether, such as shown in the prior art catheter of FIG. 5, in which two tubular members 112 and 118 are interconnected by a connecting element, such as a thread 126.

Balloon 50 is in fluid communication with an adapter 52 through a channel 54 formed in the wall of member 34 and which opens to balloon 50 at opening 55, such that balloon 50 is inflated independently of balloon 36 (when the latter is present) via adapter 52. Like balloon 24 of catheter 10, balloon 50 serves for positioning catheter 10 within the patient's urinary tract.

To this end, an indwelling catheter, e.g., catheter 110, an example of which is shown in FIG. 5, or catheter 10 according to the present invention, is attached to guiding element 32 by first inserting guiding element 32 therethrough and then inflating balloon 36 thereof. Then, guiding element 32 is guided through the urinary tract of the patient, until balloon 50 is within the bladder of the patient. Thereafter, balloon 50 is inflated and thereby anchors element 32 within the body of the patient. Subsequent pulling of element 32 such that balloon 50 is in contact with the wall of the bladder of the patient ensures accurate positioning of catheter 10 or 110 within the urinary tract thereof. Deflating both balloons 36 and 50, enables to retrieve element 32, while catheter 10 or 110 is retained in place.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

That which is claimed is:

1. A urinary catheter with a detachable guiding and positioning system, the catheter configured for insertion through the male urethra of a subject such that, in position, the catheter is in fluid communication with the bladder of the subject for conveying fluid therefrom or thereto, the male urethra generally including in serial order from its proximal to distal end, a penile meatus, a penile urethra, a urinary sphincter, and a prostate urethra, the prostate urethra being located intermediate the sphincter and the bladder, said catheter and guiding and positioning system comprising:

(a) a catheter configured for insertion into the male urethra, comprising:

an upper tubular member having opposing upper and lower end portions and a lumen with an inner wall extending therebetween, said upper end portion having at least one opening formed therein, wherein, said upper tubular member has a length such that, in position, the upper tubular member extends above the sphincter in the prostate urethra so that said upper end portion is positioned with respect to a subject's bladder to allow fluid from the bladder to enter said at least one opening formed therein;

a lower tubular member having opposing upper and lower end portions and a lumen with an inner wall extending therebetween, wherein said lower tubular member is attached to, but spatially separated a distance from, said upper tubular member, and wherein, in position in the subject, said lower tubular member is positioned below the sphincter;

(b) a tubular guide configured to be inserted into said lumen of each of said upper and lower tubular members of said urinary catheter, said tubular guide comprising:

an elongated tubular member having a length which is sufficient such that, in position inside the lumens of said catheter, said elongated tubular member axially extends from said upper tubular member through said spatially separate lower tubular member and through the penile urethra out of the subject's penile meatus;

an elongated inflatable segment disposed about a perimeter portion of said guide elongated tubular member such that said inflatable segment is operatively configured to have a first collapsed state whereby said tubular guide is detached from said upper and lower tubular members such that said tubular guide can be readily inserted into or removed from the lumens of said catheter and a second radially outwardly expanded state such that said inflatable segment affixes said guide elongated tubular member to said catheter upper and lower tubular members; and an inflation mechanism disposed externally of the subject's penile meatus, in fluid communication with said elongated inflatable segment to cause said guide elongated inflatable segment to take on said expanded configuration.

2. A urinary catheter with a detachable guiding and positioning system according to claim 1, wherein in said expanded configuration said elongated inflatable segment of said tubular guide securely abuts against said catheter upper and lower tubular element lumen inner walls, and wherein said catheter further comprises at least one connecting tube extending at least from said upper tubular element to said lower tubular element and attached to each of said upper and lower tubular elements.

3. A urinary catheter with a detachable guiding and positioning system according to claim 2, wherein said upper catheter tubular member has a first inflatable portion thereon, said catheter first inflatable portion having expandable and collapsible configurations, and wherein said catheter first inflatable portion is arranged on said upper tubular member proximate said upper end portion below said at least one opening such that when said first catheter inflatable portion is in said expanded configuration, said catheter first inflatable portion extends into the bladder and expands to anchor said catheter first inflatable portion against the bladder neck and thereby position said catheter in the subject such that said upper tubular member is positioned in the prostate urethra.

4. A urinary catheter with a detachable guiding and positioning system according to claim 3, wherein said catheter upper tubular member first inflatable portion is in said collapsed configuration during insertion of said catheter into and at removal of said catheter from the subject's urethra, and wherein said first inflatable portion is in said expanded configuration after said upper tubular member is in a desired location so that said upper end of said upper tubular member is located in the bladder a sufficient distance, and wherein said catheter first inflatable portion remains expanded in use and in contact with the subject's bladder neck while said catheter is disposed in the subject.

5. A urinary catheter with a detachable guiding and positioning system according to claim 4, wherein said catheter upper tubular member has a second inflatable portion thereon, said second inflatable portion having expandable and collapsible configurations, and wherein said second inflatable portion is arranged on said upper tubular member away from said upper end portion such that said first inflatable portion is intermediate said upper end portion and said second inflatable portion.

6. A urinary catheter with a detachable guiding and positioning system according to claim 5, wherein said catheter upper tubular member second inflatable portion has a width when expanded which is less than the expanded width of said first inflatable portion.

7. A urinary catheter with a detachable guiding and positioning system according to claim 6, wherein said catheter upper tubular member second inflatable portion has a length which is sufficient such that, in position, said catheter upper tubular member second inflatable portion extends below the bladder neck and above the sphincter and about a major portion of the length of the prostate urethra.

8. A urinary catheter with a detachable guiding and positioning system according to claim 7, further comprising two inflation flow paths in fluid communication with one of said first and second inflatable portions of said upper tubular member and said inflation mechanism disposed externally of the subject, and wherein each of said inflation paths includes at least one connecting tube longitudinally extending at least between said upper and lower members.

9. A urinary catheter with a detachable guiding and positioning system according to claim 8, wherein said first and second inflatable portions on said upper tubular member are in fluid isolation.

10. A urinary catheter with a detachable guiding and positioning system according to claim 9, wherein said upper tubular member and said lower tubular member each have an outer wall with a plurality of closed channels formed therein, one of said upper and lower closed channels forming a corresponding pair, and wherein said first and second inflation flow path includes a connecting tube and at least one of said corresponding pair of said upper and lower channels to direct an inflation medium to a desired one of said first and second inflatable portions of said catheter upper tubular member.

11. A urinary catheter with a detachable guiding and positioning system according to claim 7, wherein said second inflatable portion has a cylindrical shape with an outer diameter sufficiently sized such that when expanded said second inflatable portion resides and presses against the prostatic tissue in the prostate urethra.

12. A urinary catheter with a detachable guiding and positioning system according to claim 11, wherein said upper tubular member is configured in a plurality of different lengths and configured so that said second inflatable portion substantially corresponds to the length of the prostate urethra of the male urethra.

13. A urinary catheter with a detachable guiding and positioning system according to claim 11, wherein said upper tubular member is configured with a length which is between about 4–10 cm.

14. A urinary catheter with a detachable guiding and positioning system according to claim 7, wherein, when said catheter upper tubular member first and second inflatable portions are expanded, said catheter upper tubular member has a cross sectional profile which widens from said upper end tip to an arcuately bulbous configuration at said first inflatable portion, narrows intermediate said first and second inflatable portions, and then widens at said second inflatable portion to an elongated linear configuration, and wherein said first and second inflatable portions are in fluid communication.

15. A urinary catheter with a detachable guiding and positioning system according to claim 5, wherein, when said upper tubular member first and second inflatable portions are expanded, said catheter upper tubular member has a cross sectional profile which widens from said upper end tip to an arcuately bulbous configuration at said first inflatable portion, narrows intermediate said first and second inflatable portions, and then widens at said second inflatable portion to an elongated linear configuration, and wherein said first and second inflatable portions are in fluid isolation.

16. A urinary catheter with a detachable guiding and positioning system according to claim 5, wherein said second inflatable portion of said upper tubular member is configured to thermally ablate the prostate by delivering heated fluid at said second inflatable portion, and wherein said second inflatable portion is configured to withstand fluid heated to a temperature in the range of between about 55° C. to 80° C.

17. A urinary catheter with a detachable guiding and positioning system according to claim 5, wherein said second inflatable portion of said upper tubular member is permeable to medicaments and wherein, in position, said second inflatable portion is expanded by inflating said second inflatable portion with a liquid comprising medicaments to thereby deliver same to the subject.

18. A urinary catheter with a detachable guiding and positioning system according to claim 4, said catheter further comprising at least one inflation flow path in fluid communication with said first inflatable portion of said upper tubular member and said inflation mechanism disposed externally of the subject, and wherein said at least one inflation flow path includes said at least one connecting tube.

19. A urinary catheter with a detachable guiding and positioning system according to claim 18, wherein said catheter upper tubular member and said lower tubular member each have an outer wall and at least one corresponding closed channel formed therein, and wherein said at least one inflation flow path includes said at least one connecting tube and at least one of said upper and lower channels to direct an inflation medium to said first inflatable portion.

20. A urinary catheter with a detachable guiding and positioning system according to claim 4, wherein said catheter at least one connecting tube is sized and configured to define an enclosed inflation medium delivery channel which is in fluid communication with said first inflatable portion on said upper tubular member, wherein in position in the subject, said at least one connecting tube extends through the sphincter, and wherein said at least one connecting tube is configured so as to allow the sphincter to close naturally with said at least one connecting tube extending therethrough.

21. A urinary catheter with a detachable guiding and positioning system according to claim 1, wherein said tubular guide has a second inflatable portion which is distal to said tubular guide elongated inflatable segment such that, in position, said tubular guide second inflatable portion is located above said catheter upper tubular member, wherein said guide second inflatable portion has expandable and collapsible configurations, and wherein, when in the expanded configuration and in position in the subject, said tubular guide second inflatable portion extends into the bladder a sufficient distance and expands to anchor said guide second inflatable portion against the bladder neck and thereby hold said catheter and said guide in a desired position in the subject relative to the bladder of thereof.

22. A urinary catheter with a detachable guiding and positioning system according to claim 21, wherein said tubular guide first inflatable segment and second inflatable portion are separately inflatable via different inflation pathways extending between a respective one of said first inflatable segment and second inflatable portion and said inflation mechanism.

23. A urinary catheter with a detachable guiding and positioning system according to claim 22, wherein said guide first elongated inflatable segment is in the expanded configuration during insertion of the catheter and guide through the urethra, and said guide second inflatable portion is in the collapsed position, and wherein said second inflatable portion is in said expanded configuration after said guide and catheter are in a desired position relative to the bladder.

24. A urinary catheter with a detachable guiding and positioning system according to claim 21, wherein a distal end portion of said tubular guide includes at least one opening formed therein, and wherein said tubular guide includes a longitudinally extending lumen therein such that said at least one opening and said lumen are in fluid communication and configured to allow fluid to drain from the bladder therethrough.

25. A urinary catheter with a detachable guiding and positioning system according to claim 1, wherein said tubular guide has a closed distal end.

* * * * *